United States Patent [19]

Beurrier

[11] Patent Number: 5,308,353
[45] Date of Patent: May 3, 1994

[54] SURGICAL SUTURING DEVICE

[75] Inventor: Henry R. Beurrier, Far Hills, N.J.

[73] Assignee: Merrimac Industries, Inc., West Caldwell, N.J.

[21] Appl. No.: 938,923

[22] Filed: Aug. 31, 1992

[51] Int. Cl.$^5$ .............................................. A61B 17/00
[52] U.S. Cl. ..................................... 606/144; 606/139;
606/223; 112/80.03; 112/169
[58] Field of Search ................ 606/139, 144, 145, 147,
606/148, 185, 187, 222-227; 112/80.03, 169

[56] References Cited

U.S. PATENT DOCUMENTS

| | | | |
|---|---|---|---|
| 4,557,265 | 12/1985 | Andersson | 606/144 |
| 4,747,358 | 5/1988 | Moll et al. | 112/169 |
| 4,899,746 | 2/1990 | Brunk | 112/169 |

FOREIGN PATENT DOCUMENTS

| | | | |
|---|---|---|---|
| 0835429 | 6/1981 | U.S.S.R. | 606/144 |
| 0018602 | of 1908 | United Kingdom | 606/139 |
| WO/8603396 | 6/1986 | World Int. Prop. O. | 606/224 |

Primary Examiner—Stephen C. Pellegrino
Assistant Examiner—Jeffrey A. Schmidt
Attorney, Agent, or Firm—Pennie & Edmonds

[57] ABSTRACT

A mechanical apparatus for suturing biological tissue, or ligating a biological tube or duct, in remote or otherwise inaccessible areas such as internal body cavities. The suturing apparatus includes an elongated housing, a head assembly pivotally mounted to the elongated housing capable of independent articulation, a continuous loop belt mounted within the elongated housing and head assembly for circulation therein, an arcuate needle mounted in the head for 360° rotation having a plurality of projecting means for engaging the continuous loop belt, means for articulating the head assembly from a position outside a patient's body, and means for circulating the continuous loop drive belt. A kit for suturing biological tissue, or ligating a biological tube or duct, comprising a cannula and a mechanical apparatus for suturing or ligating as described above, configured and dimensioned to be slidingly received in the cannula.

21 Claims, 10 Drawing Sheets

SURGICAL SUTURING DEVICE

TECHNICAL FIELD

The present invention generally relates to surgical instruments, and more particularly, to suturing devices.

BACKGROUND OF THE INVENTION

Various forms of suturing devices are known in the art, and those which utilize a curved needle are particularly relevant to the present invention. For example, U.S. Pat. Nos. 4,027,608 and 4,235,177 to Arbuckle, 4,406,237 to Eguchi et al., 4,417,532 to Yasukata, and 4,440,171 to Nomoto et al. describe suturing devices that use a reciprocating curved needle and means for looping and/or securing a suture thread; U.S. Pat. No. 4,557,265 to Andersson, describes a suturing device and method for moving an arcuate needle in a closed path through opposite edges of a tissue incision to complete a suture; U.S. Pat. No. 4,899,746 to Brunk describes a suturing device incorporating a curved needle into a motor driven cassette; and, U.K. Patent No. 18,602 to Mitchell describes a suturing device utilizing an arcuate needle having two recesses on remote ends of the needle which are capable of being engaged by two mating tooth-like projections on the surface of a band.

There are various drawbacks, however, with the prior art. For instance, the apparatuses described in Arbuckle, Eguchi, Yasukata and Nomoto use a reciprocating needle. These devices therefore require an added mechanism for looping and/or securing the suture thread. The added mechanism, however, unnecessarily increases the size of the suturing device making it impractical for suturing in small or crowded areas, such as, internal body cavities. Notwithstanding that problem, the added mechanism is also less efficient for tying a suture knot when compared to the semi-automatic knot tying capabilities of the present invention.

There are prior art devices which do not require the added thread looping mechanism. In general, these devices utilize a fully rotating arcuate needle. These instruments, however, pose a potential health risk to surgery patients. For instance, instruments as described in Andersson and Brunk both utilize friction rollers to drive a curved suturing needle through biological tissue. The suturing needle, however, does not positively engage the friction rollers (and vice versa), and therefore, the needle is not prevented from slipping and embedding in a patient. This most likely occurs when the needle encounters a friction force from the tissue being sutured greater than the friction force of the rollers driving the needle. Needle slippage can be avoided by ensuring positive engagement of the needle with a driving mechanism like the apparatus described in Mitchell. However, even the Mitchell apparatus, poses the same risk of embedding the needle in a patient where either tooth on the band fails to engage with its sole mating recess on the needle. Therefore, as evidenced by the prior art, there is a need for a suturing apparatus which overcomes these apparent problems.

Also known in the art are suturing instruments for arthroscopic surgery, laparoscopic procedures, and other small-scale surgical applications. For example, U.S. Pat. Nos. 1,822,330 to Ainslie, 3,871,379 to Clarke, 4,597,390 and 4,621,640 to Mulhollan et al., 4,781,190 to Lee, 4,923,461 and 4,957,498 to Caspari et al., 5,047,039 to Avant et al., and 5,059,201 to Asnis describe devices related to these medical procedures. None of these devices, however, utilize an arcuate suturing needle. As a result, these devices are bulkier, less efficient and less accurate for performing such procedures than the present invention described herein.

SUMMARY OF THE INVENTION

In light of the aforementioned drawbacks with the prior art, it is a particular objective of this invention to prevent the suture needle from slipping. To achieve this objective the present invention comprises a body member wherein there is a continuous loop belt mounted for circulation, and an arcuate needle mounted for 360° rotation, having a plurality of spaced projecting means for positively engaging the belt. At least two of the projecting means engage the belt at all times. By satisfying the present objective the present invention is an improvement over prior art instruments for suturing biological tissue, or ligating a biological tube or duct.

Because the needle advances through its suturing rotation when the drive belt passes over the needle, the body member also contains means for circulating the continuous loop belt. The means for circulating the belt includes an engine and a coupler. The engine has a reciprocating piston slideably mounted within a cylinder which transforms a flow of pressure fluid (into the cylinder) into compression of a spring. Driving force is supplied by the release of the compressed spring. The coupler comprises an elongated coupling sleeve having a plurality of projecting means for engaging the drive belt. This allows the drive belt to be connected to the engine, and more specifically, to the compressed spring.

An additional objective of the present invention is to provide a suturing apparatus that allows for suturing or ligating in remote locations or otherwise inaccessible areas, such as internal body cavities. To satisfy this objective, the body member of the present invention comprises an elongated housing and a head assembly. The head assembly is mounted on the end of the elongated housing and is capable of independent articulation from the housing, as described below. Additionally, the present invention uses a fully rotating arcuate needle. Therefore, a suture knot can be semi-automatically tied by prearranging the suture thread on the head assembly before suturing, followed by simple manual manipulation of the ligature material after the thread has been installed in the biological tissue. This eliminates the need for an additional looping mechanism (associated with reciprocating needle devices) and further decreases the size of the present invention. As a result of these refinements, the suturing instrument described herein is dimensioned and configured to be inserted through a trocar cannula which has been previously inserted into an internal body cavity of a patient.

It is a further object of the present invention to enable a user to position the head assembly (containing the suture needle) from a location outside a patient's body, even when the suturing device is inserted within an internal cavity of a patient. The present invention satisfies this objective by pivotally mounting the head assembly to the elongated housing for independent articulation. A plurality of sprocketed belts provides means for articulating the head assembly and needle contained therein.

An additional object of the present invention is to provide a kit for suturing biological tissue or agating a biological tube or duct. The kit includes a sealed container filled with a lubricating substance, a trocar including a cannula adapted to sealingly receive a stylet (also included) and the suturing device as described herein, configured and dimensioned to be inserted into the cannula.

An added benefit of the present invention is that it reduces a patient's time for recovery by limiting the cutting and carnage of the patient's body associated with internal surgical procedures. For instance, an internal abdominal operation merely requires a surgeon to insert the suturing apparatus described herein through a cannula located in the patient's abdominal wall. The surgeon can observe the area to be sutured or ligated through a viewing device inserted through another cannula. Other operating tools can be similarly inserted into the body cavity. This arrangement eliminates cutting open the patient's abdomen, and ultimately reduces the patient's time for recovery.

DETAILED DESCRIPTION OF THE PREFERRED EMBODIMENT

Figure 1:
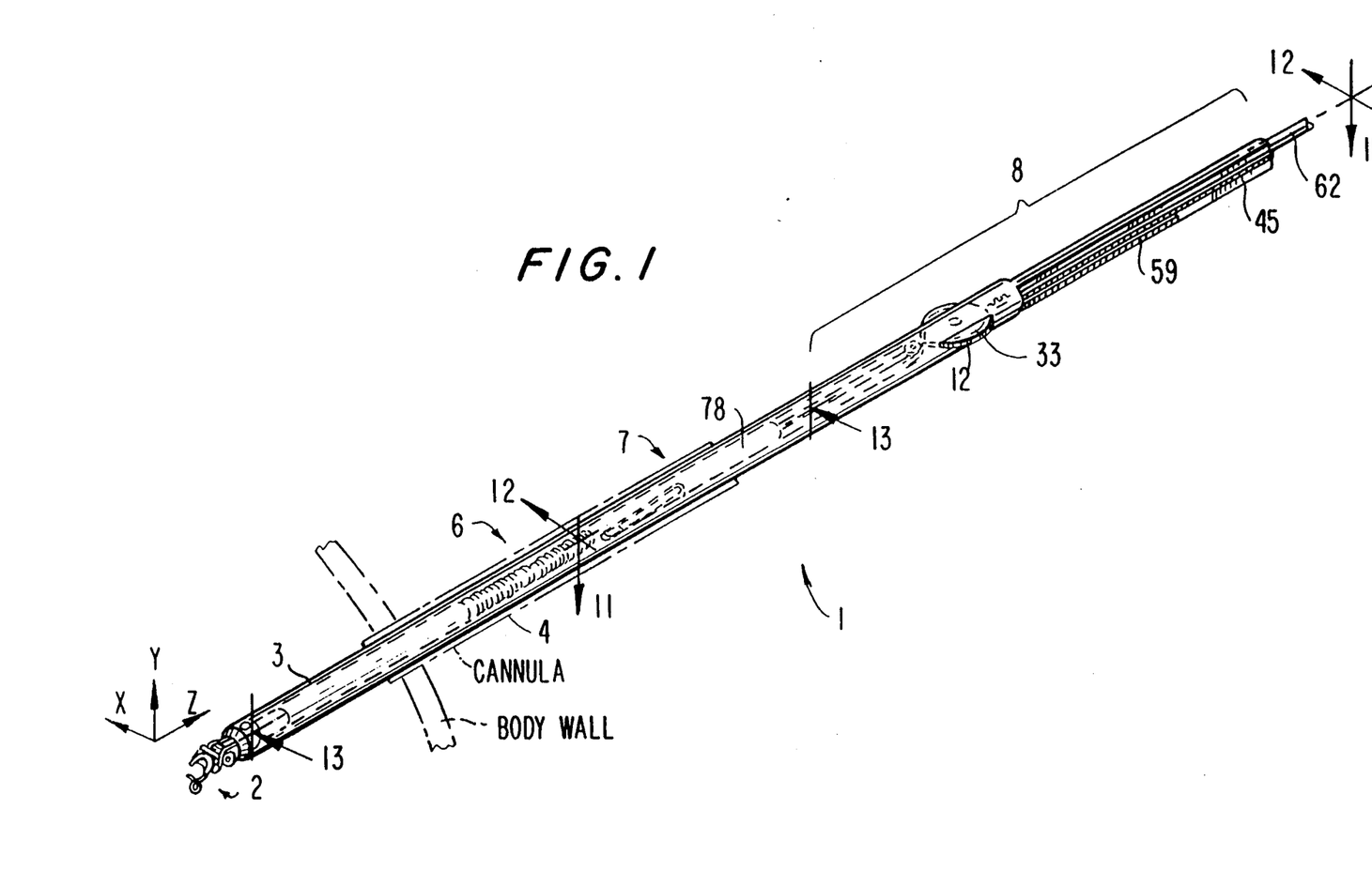
FIG. 1 is an overall perspective view of the surgical suturing device of the present invention.
Figure 2:
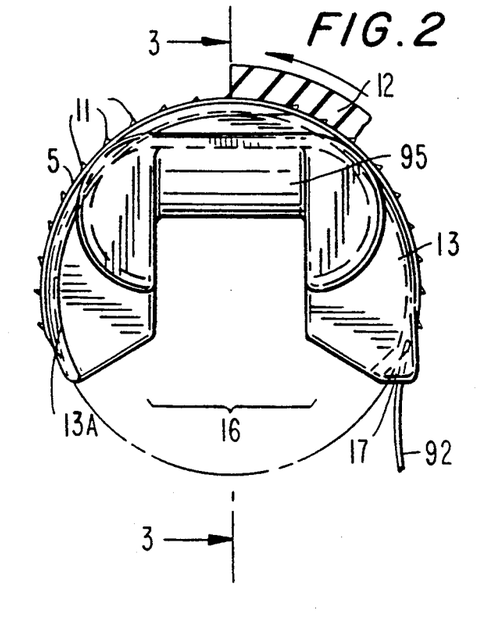
FIG. 2 is a partial front view of the saddle and the barbed arcuate suturing needle located within the head of the surgical suturing device.

Referring to FIG. 1, surgical suturing device 1 has four basic sections: a head 2, an engine 6, a coupler 7, and a drive belt management/head articulation section 8. These four sections are aligned such that suturing device 1 can be inserted S into a cannula 4 of a known trocar, such as described in U.S. Pat. No. 4,177,814 which is incorporated herein by reference thereto. This permits a user of suturing device 1 to perform suturing procedures inside a patient's internal cavities, or in other remote locations.

It is to be understood that moving parts described and illustrated have sufficient clearance to move relative to an adjacent part without incurring unwanted friction or seizing therebetween. This is particularly relevant to the figures where several adjacent moving parts are depicted as touching one another for the sake of clarity in the drawings.

Referring to FIGS. 2-5, suturing device 1 installs a suture by rotating an arcuate suturing needle 5 through biological tissue to be sutured. Arcuate suturing needle 5 is mounted for 360° rotation within head 2, and preferably has a three-edge cutting point, although alternative shapes are possible. The needle is preferably made of stainless steel, however, many a variety of surgical grade materials may be used as will be appreciated by those skilled in the art. Needle 5 also has a series of radially outward projecting barbs 11, which are angled, preferably acutely, to the rear (trailing thread end) of needle 5. These barbs 11 are formed either at least substantially around the outer perimeter of the needle, or in groups around the perimeter. The angle of barbs 11 facilitates engagement of needle 5 with a needle drive belt 12 which passes over needle 5 in the direction of the needle's leading point. This causes the needle 5 to rotate when the belt 12 is moved forward. Although needle barbs 11 penetrate belt 12 they are oriented to pass freely through any biological tissue to be sutured. Preferably, the barbs are closely spaced and positioned such that at least two barbs contact the belt at all times during rotation of the needle to ensure constant positive engagement between the needle and the belt.

Figure 3:
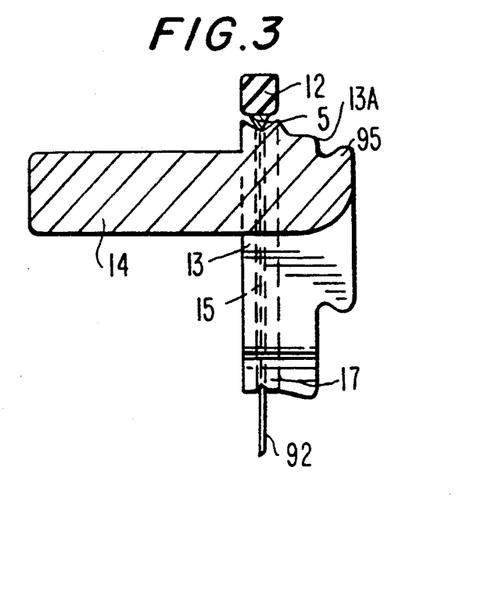
FIG. 3 is a partial cross-sectional side view of the saddle and the barbed arcuate suturing needle taken along line 3—3 of FIG. 2 and also depicting the needle drive belt engaged with the needle.
Figure 9:
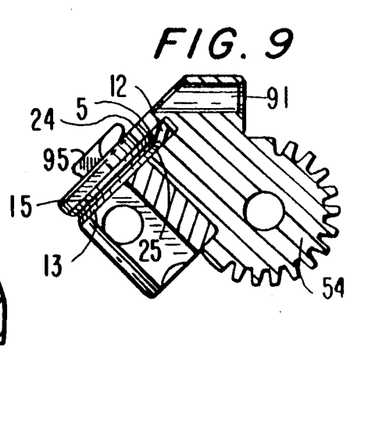
FIG. 9 is a partially sectioned side view of the head (having a complete side view of the saddle) of the surgical suturing device taken along line 9—9 of FIG. 7.

As needle 5 rotates, it is supported on a semi-circular saddle 13. Saddle 13 extends around an arc of slightly more than 180° so needle 5, which also extends around an arc of more than 180°, is always in sliding contact with the saddle. Referring to FIGS. 3 and 9, saddle 13 is sloped inward towards a needle guide groove 15 formed in the saddle along its circumference. Groove 15 ensures that needle 5 is retained in the saddle as it travels through its arcuate path. Preferably, groove 15 is the same shape as the cross-sectional shape of needle 5, allowing needle 5 to fit snugly into the groove. As best seen in FIGS. 3 and 9, groove 15 is triangular in shape to match the preferred triangular shape of needle 5.

Figure 4:
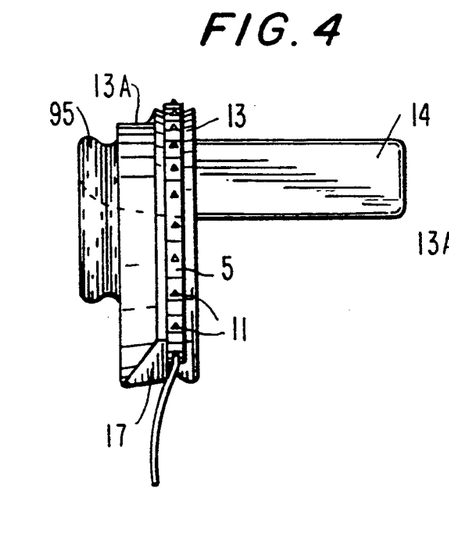
FIG. 4 is a side view of the saddle and barbed arcuate suturing needle that is located within the head of the surgical suturing device.

Referring to FIGS. 3 and 4, saddle 13 is supported on mounting post 14 which extends perpendicularly from saddle 13. Preferably, post 14 is rectangular in shape (although any shape compatible with the design of head 2 can be used) and can be either riveted or cemented within head 2. Alternatively, post 14 can be screwed into or otherwise temporarily secured to head 2 if a removable saddle 13 is preferred; for instance, to facilitate changing or loading a new needle 5 by allowing the needle to be placed directly on saddle 13, as described below.

Referring back to FIGS. 2–5, as needle 5 rotates it passes across opening 16 formed in the lower portion of the saddle on the opposite side of where the needle and saddle mate. Opening 16 accommodates biological tissue to be sutured. Needle 5 reenters saddle 13 at needle entrance 17 which is designed to funnel needle 5 back into groove 15. By maintaining needle 5 in needle guide groove 15, control and accurate positioning of needle 5 can be preserved, regardless of the forces encountered by the needle as it passes across opening 16 and through any biological tissue to be sutured.

Referring to FIGS. 6–8 and 10, needle 5 rotates across opening 16 when continuous loop needle drive belt 12 passes over and engages needle 5 within head 2. Needle drive belt 12 is made of a flexible yet stretch resistant composite of materials having a pliable, tear resistant exterior which is penetratable by barbs 11, and a strong non-elastic core. The belt can be constructed of a variety of materials which satisfy the foregoing characteristics and are appreciated by those skilled in the art. Preferably belt 12 has a square cross-sectional shape, although it can be circular, elliptical, rectangular, or almost any shape which is compatible with the suturing device's internal mechanism.

Figure 10:
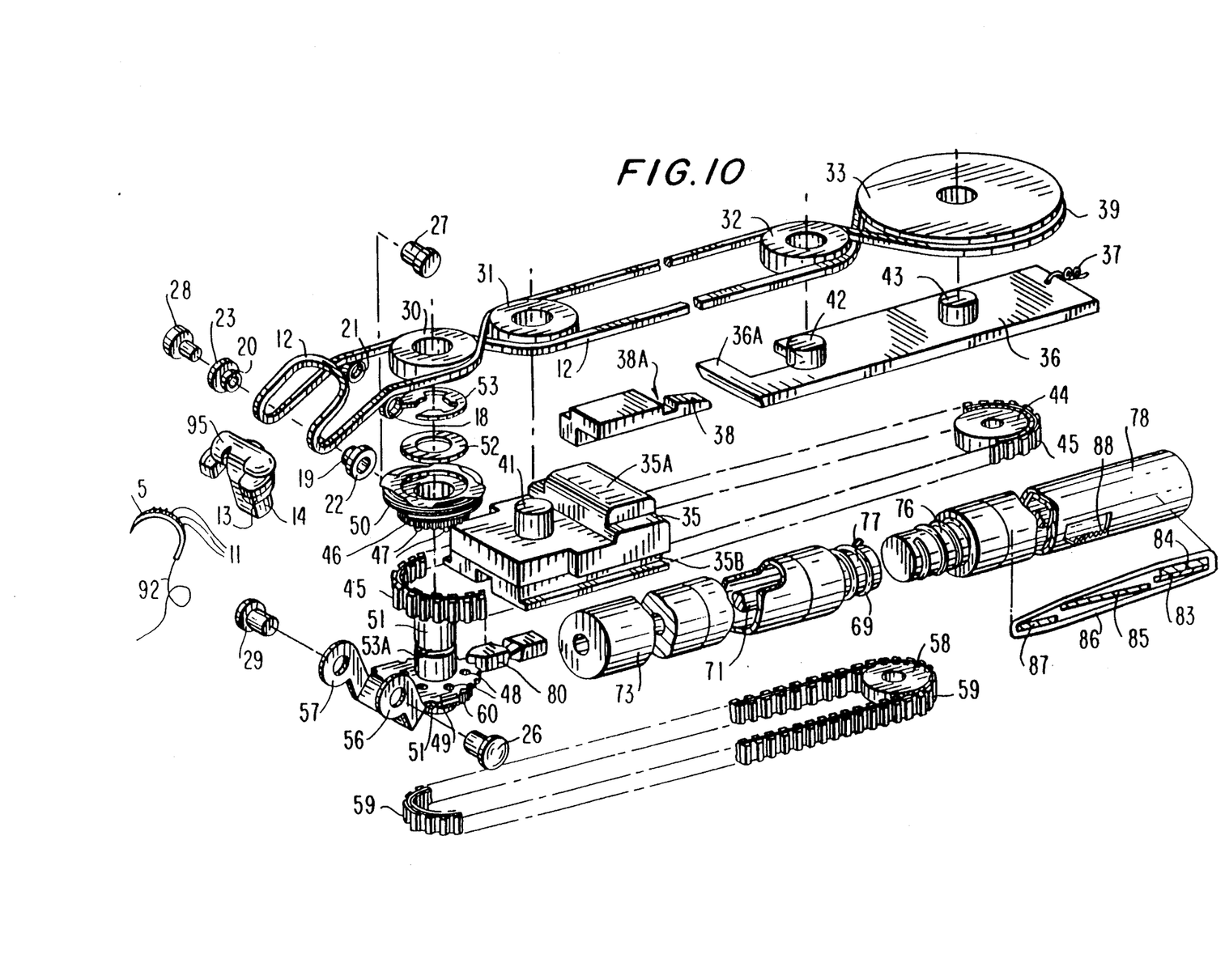
FIG. 10 is an exploded view of the surgical suturing device of the present invention with the outer body member removed.

Circulation of drive belt 12 through head 2 is directed by pulleys 18–21, and flanges 22 and 23 (see FIG. 10). Pulleys 18 and 21 are rotatably mounted on axles 26 and 29, respectively. Pulleys 19 and 20, as well as flanges 22 and 23, are rotatably mounted on axles 27 and 28, respectively. As belt 12 enters head 2, belt 12 engages pulley 18. Pulley 18 redirects belt 12 under pulley 19, whereby the belt makes a 180° turn and is redirected over needle 5. Flange 22 facilitates engagement of belt 12 with needle barbs 11 by pressing the belt 12 against the needle barbs near needle entrance 17. Front wall 24 and rear wall 25 of device 1 (see FIG. 8) maintain belt 12 over needle 5 as the belt extends over, and is engaged with, the needle sliding on saddle 13. As belt 12 disengages from needle barbs 11, belt 12 encounters a second flange 23 (FIG. 6), which helps maintain belt 12 on pulley 20 as it passes therearound. Belt 12 passes under pulley 20, up and over pulley 21, before exiting head 2 and passing down the length of suturing device 1.

In the preferred embodiment illustrated in the drawings, needle 5 lies in a plane which is essentially perpendicular to the plane in which pulleys 18–21 lie. In order to minimize the cross-sectional area of head 2 it is contemplated, in an alternative embodiment, that needle 5 and pulleys 18–21 may lie in the same or parallel planes.

Figure 7:
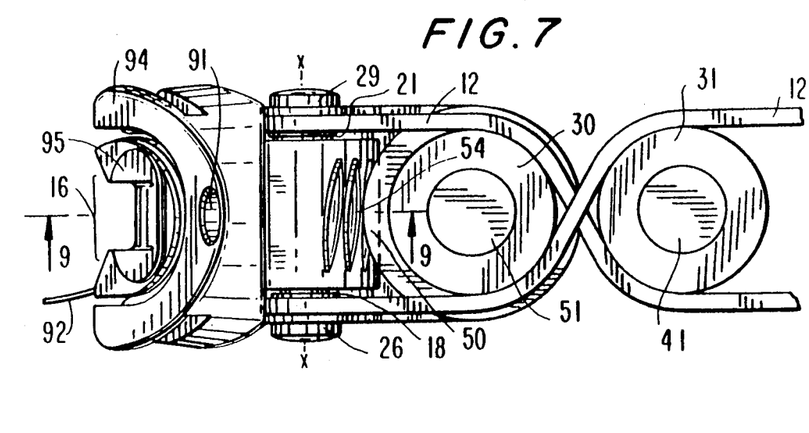
FIG. 7 is a partial plan view of the head of the surgical suturing catheter.
Figure 8:
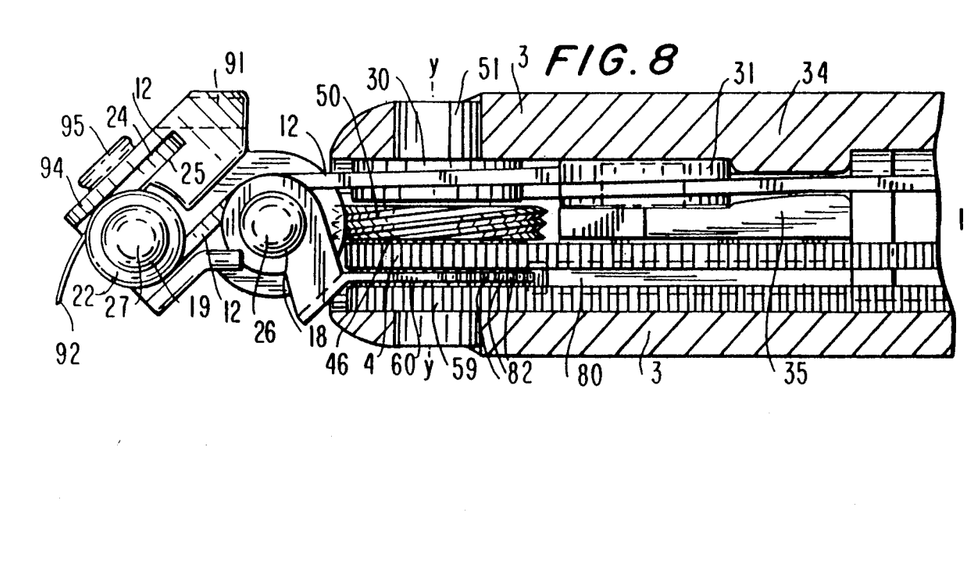
FIG. 8 is a partially sectioned side view of the head of the surgical suturing device.

As shown in FIGS. 8 and 10, drive belt 12 is directed through the remainder of device 1 by pulleys 30–33, and raised surfaces 34 and 35. Referring to FIGS. 7, 8 and 10, as drive belt 12 exits head 2 it engages pulley 30 and then crosses itself between pulleys 30 and 31. Pulleys 30 and 31 are rotatably mounted on axles 51 and 41, respectively. After pulley 31, belt 12 encounters two protruding surfaces 34 and 35 which stabilize belt 12 as it extends down the length of suturing device 1. Protruding surfaces 34 and 35, in conjunction with raised partition 35A, are preferably spaced to form a gas-tight seal around belt 12 (and belts 45 and 59). This restricts the escape of gases or pressure in the body cavity, through the body of suturing device 1, during suturing procedures. Similar provisions are taken to seal the passages accommodating belts 45 and 59.

Figure 11:
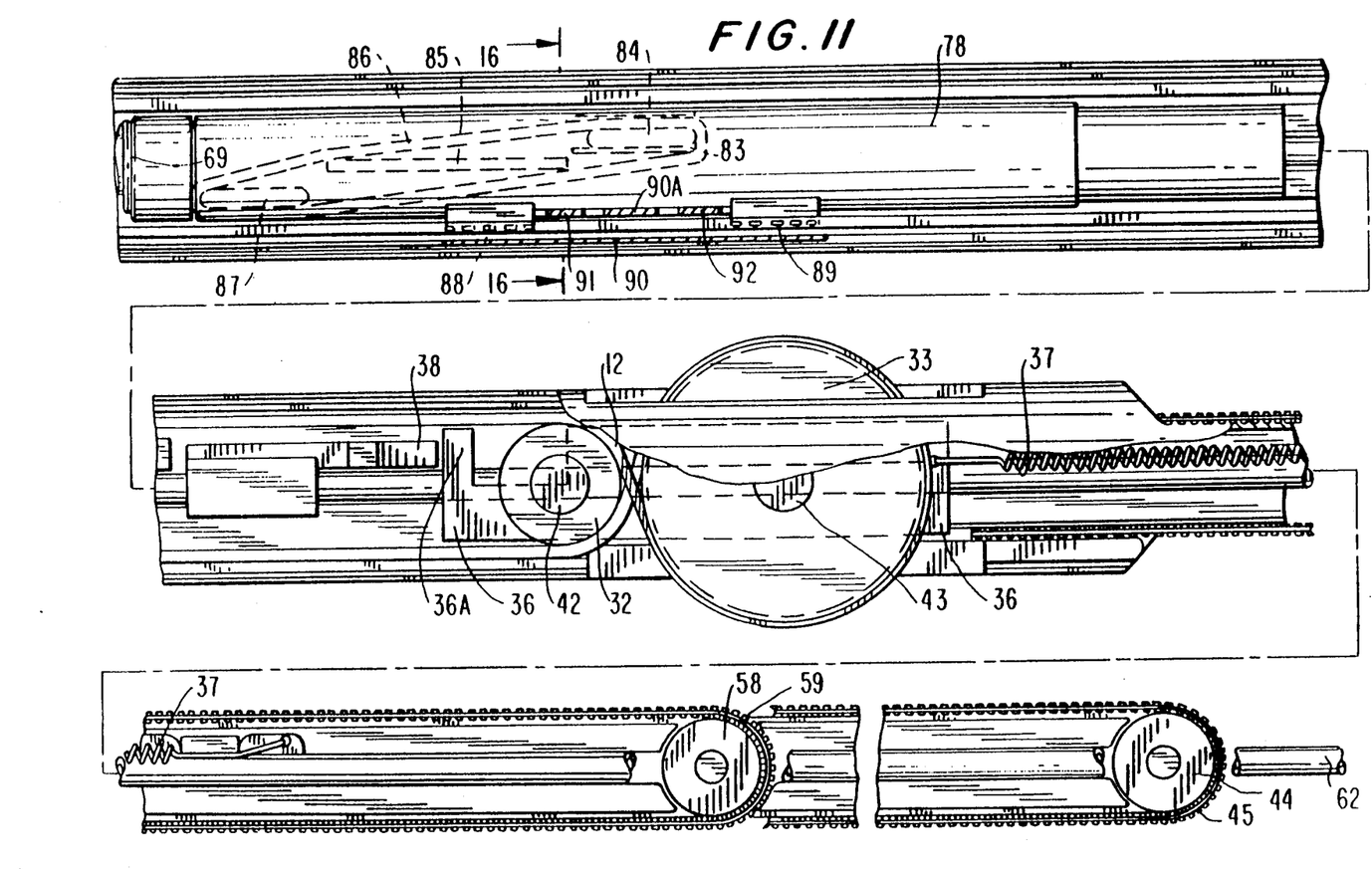
FIG. 11 is a sectional top view of the distal end of the surgical suturing device taken along line 11—11 of FIG. 1.
Figure 12:
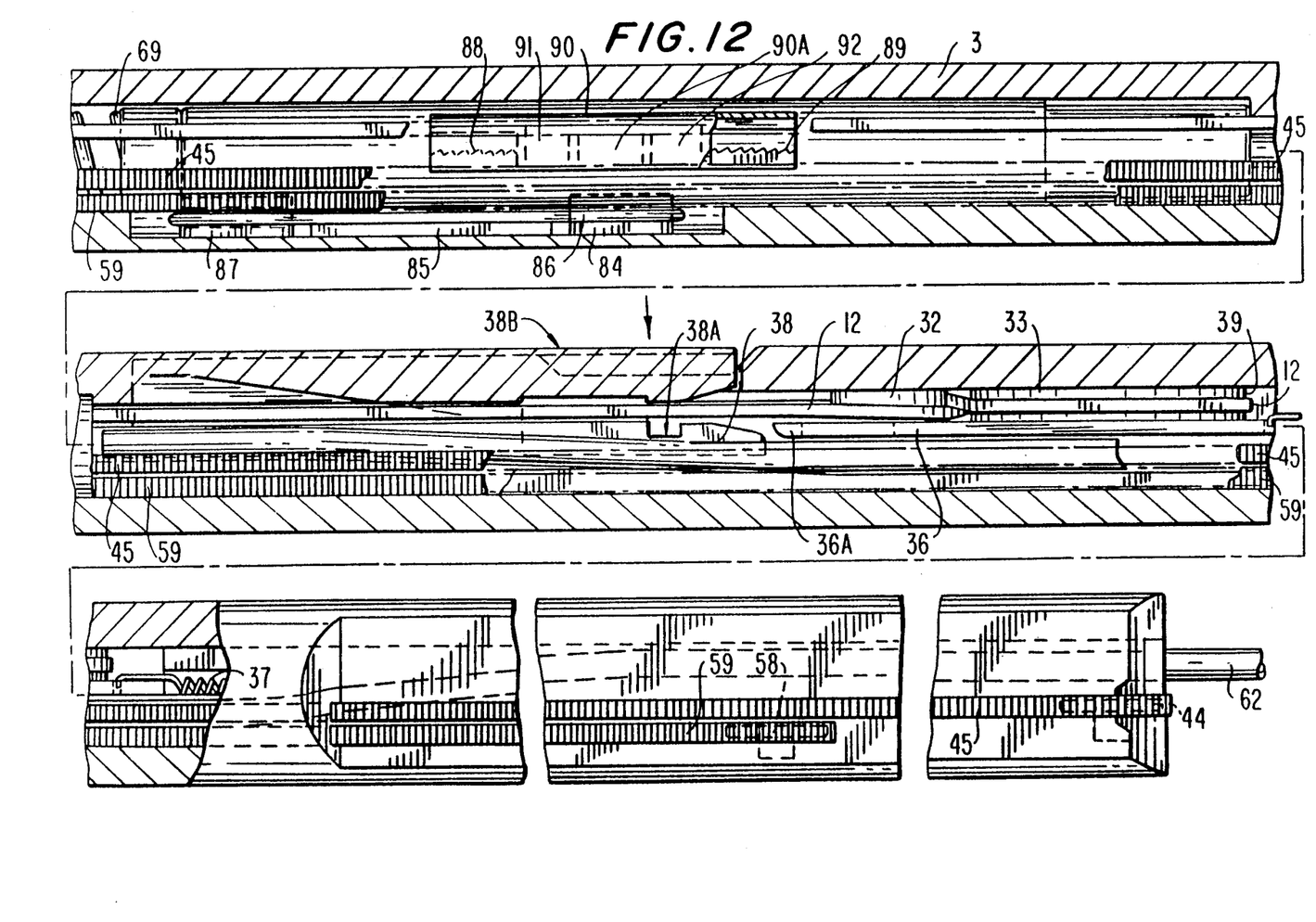
FIG. 12 is a sectional side view of the distal end of the surgical suturing device taken along line 12—12 of FIG. 1.

Referring to FIGS. 10, 11 and 12, as belt 12 approaches the proximal end of device 1 it initially engages pulley 32 before crossing itself again between pulleys 32 and 33. Pulleys 32 and 33 are rotatably mounted on axles 42 and 43, respectively, which in turn are mounted on a carriage 36, which is explained below. Pulley 32 facilitates engagement of belt 12 with pulley 33 by maintaining the belt within flanges 39 formed on the outer circumference of pulley 33. As best shown in FIGS. 1 and 11, pulley 33 is larger than the other pulleys utilized in the drive belt management system, and extends outside of housing 3. This allows belt 12 to be gripped directly by a user as a manual control for positioning needle 5 in saddle 13.

Referring again to FIGS. 10, 11 and 12, carriage 36 is slideably mounted in housing 3, and further secured to the housing by tension spring 37. The primary purpose of spring 37 is to bias the carriage and the pulleys in the proximal direction and thus ensure a constant tension in belt 12. Maintaining a constant tension in the belt eliminates slack and prevents it from dragging on the inside surface of housing 3, which would hinder the belt's movement. More importantly, the application of constant tension facilitates proper engagement of belt 12 with needle barbs 11 on needle 5 in the area over saddle 13 at the distal end of device 1. In order to temporarily relieve tension on belt 12, for example, when a new needle 5 is installed, carriage 36 can be slid forward by pushing pulley 33 distally. The carriage is temporarily secured on latch 38 with arm 36A received in notch 38A. A lever 38B is provided in the top portion of housing 3 which forces latch 38 downward and releases arm 36A from notch 38A when the lever is depressed (FIG. 12).

Referring to FIGS. 3 and 4, changing or loading a new needle 5 into saddle 13 is accomplished by placing the needle on loading surface 13A with the leading point of the needle facing needle entrance 17. While maintaining needle 5 essentially on surface 13A, the leading point of needle 5 must be manually directed into needle entrance 17 as belt 12 is manually rotated. Continuous operation of the belt will carry needle 5 completely onto saddle 13 after which the proper starting position of the needle can be ascertained. Alternatively, saddle 13, supported on post 14, can be designed such that it is removable from head 2. This would allow needle 5 to be placed directly on saddle 13 which can then be reattached to head 2 ready for use.

As explained above, needle 5 engages belt 12 and is advanced through a 360° suturing rotation by movement of belt 12 through the suturing device. In order to advance the belt automatically, engine 6 is provided in housing 3 slightly distally of the midpoint of the device 1 (see FIG. 1).

Figure 13:
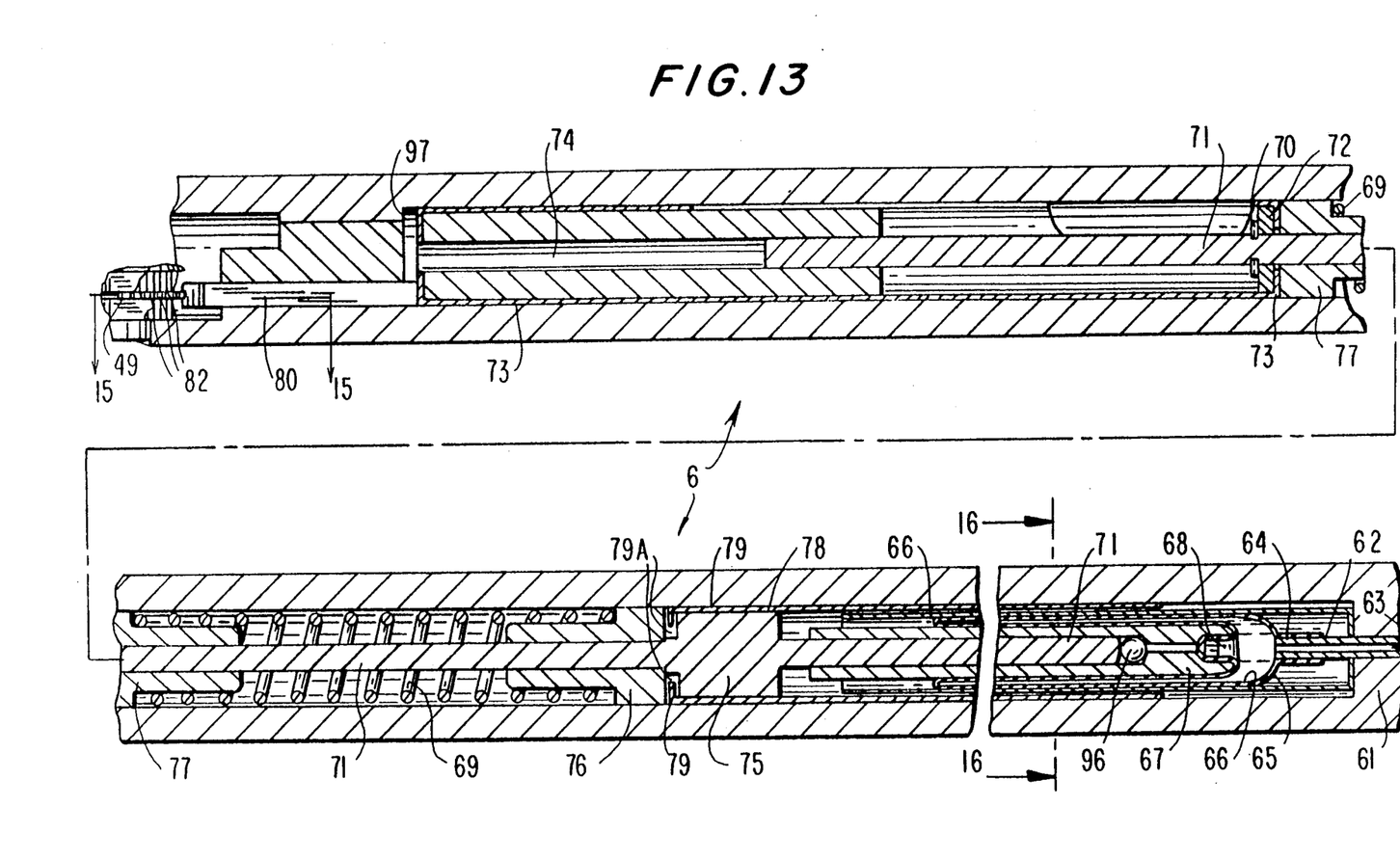
FIG. 13 is a sectional side view of the surgical suturing device, taken along line 13—13 of FIG. 1, showing the engine before compression of the spring.
Figure 14:
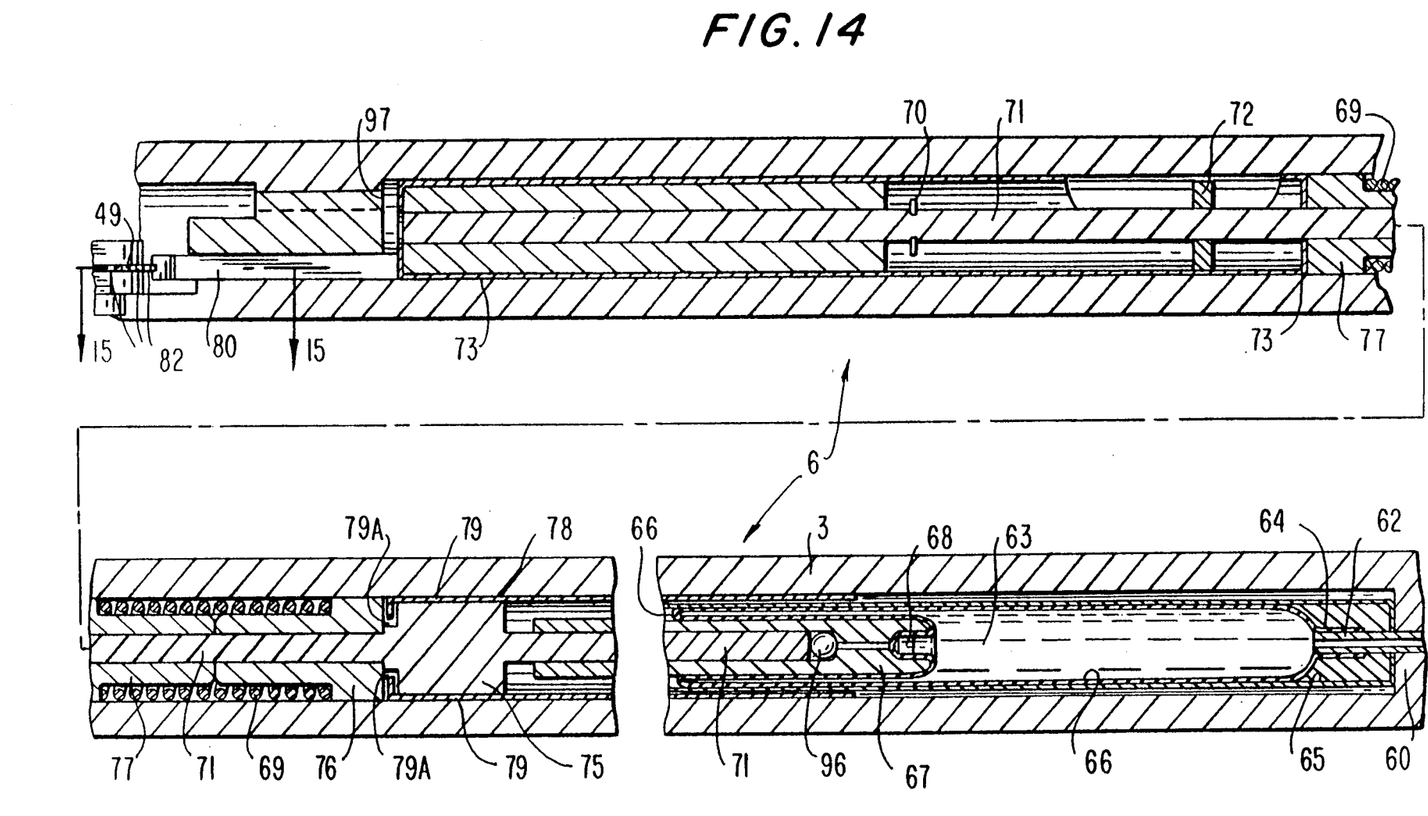
FIG. 14 is a view similar to FIG. 13, except that it depicts the engine after compression of the spring.

Referring specifically to FIGS. 13 and 14, it can be seen that engine 6 is mounted inside housing 3 between two bulkheads 61 and 97. The engine is activated by fluid pressure. Any medically suitable lubricating fluid may be used as a hydraulic medium. The pressure fluid is provided to the engine by depressing a foot operated pump (not shown) that is connected to the engine by a single small diameter hydraulic tube 62. The design of such a device is within the ability of persons skilled in the art.

Tube 62 communicates with engine 6 through opening 64 located in the proximal end of cylinder 65. Cylinder 65 is lined with a rolling diaphragm 66 which is fixed at opening 64 to cylinder 65. Rolling diaphragm 66 extends from opening 64 into the open cavity of cylinder 65 and folds back upon itself between the inner wall of cylinder 65 and the outer wall of piston 67. Rolling diaphragm 66 is fixed at its other end to the proximal end of piston 67 at connection point 68. Rolling diaphragm 66 not only contains the flow of hydraulic pressure fluid 63 emitted into cylinder 65, but also allows piston 67 to reciprocate within the cylinder. For orientation it should be appreciated that the piston-cylinder arrangement is disposed substantially within coupling sleeve 78. Coupling sleeve 78 forms part of coupler 7, which couples the engine to drive belt 12. The coupler and sleeve are explained in detail below.

As shown in FIG. 13, engine 6, and more specifically, spring 69 are shown in a prespring compression stage. Compression of the spring (as shown FIG. 14) is accomplished by the arrangement of piston 67, a thrust bearing 96, a connecting rod 71, a connecting rod shoulder enlargement 75, and two spring bushings 76 and 77. Pressure applied to piston 67, by the flow of pressure fluid 63 into cylinder 65 (as described above), forces the piston to move distally within the cylinder. Movement of piston 67 is transmitted to connecting rod 71 through thrust bearing 96. Near the center of connecting rod 71 is a shoulder enlargement 75 which transfers movement of connecting rod 71 to spring bushing 76 slideably mounted on the connecting rod. Mounted on a shoulder formed on bushing 76 is the proximal end of spring 69. The distal end of spring 69 is likewise mounted on a shoulder of a second spring bushing 77 which is held stationary against the proximal end of an engine housing 73. Therefore, as shown in FIG. 14, as fluid pressure is applied to engine 6, movement of connecting rod 71 and shoulder enlargement 75 is transmitted to spring bushing 76 which compresses spring 69 against bushing 77, until both bushings come into contact with one another.

The work of compressed spring 69 is converted into rotation of needle 5 by coupler 7. During the spring compression cycle, movement of connecting rod 71 actuates coupler 7 to engage drive belt 12 just as the spring reaches its compressed state (as shown in FIG. 14). Therefore, when fluid pressure is suitably reduced in cylinder 65 (by the release of foot pedal pressure), the engine begins its power stroke with spring 69 extending and drive belt 12 drawn forward by the spring through coupler 7. As described above, movement of drive belt 12 causes needle 5 to move through its suturing rotation.

Referring to FIGS. 11 and 13, coupler 7 engages drive belt 12 through coupling sleeve 78 provided with toothed belt engaging tabs 88 and 89. Coupling sleeve 78 is keyed to the translational movement of connecting rod 71 by an inward directed flange 79 (FIG. 13) fitted within an annular space between bushing 76 and shoulder enlargement 75. However, flange 79 has sufficient clearance 79A from connecting rod 71 to allow the sleeve to rotate freely. Rotation of sleeve 78 allows the toothed tabs 88 and 89 to engage and disengage drive belt 12 during the various cycles of engine 6 as explained below.

Rotation of sleeve 78, in response to linear motion of connecting rod 71, is created by an arrangement of guiding tabs and posts and an elastic band. The general location of tab 83, posts 84 and 87, rail 85 and band 86 can be seen, for example, in FIGS. 11 and 16.

Figure 16:
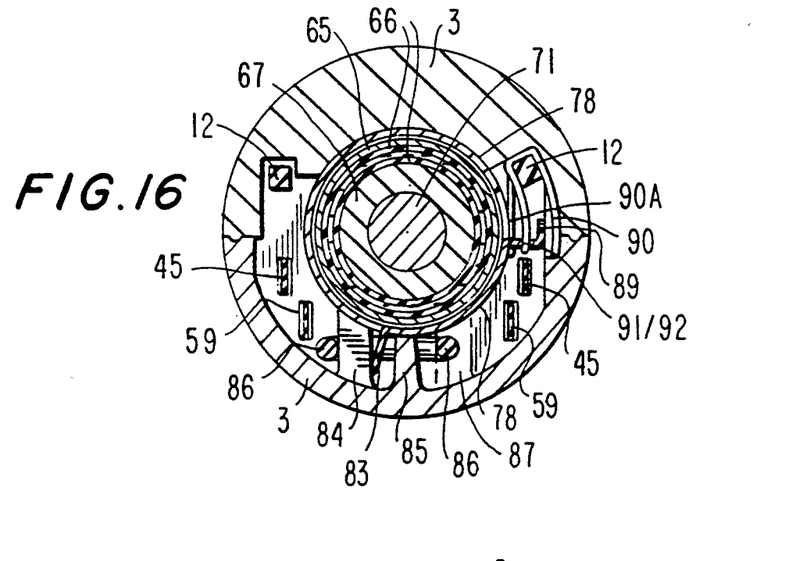
FIG. 16 is a cross-sectional view through the coupler of the surgical suturing device, taken along line 16—16 of FIG. 13, before the drive belt is coupled to the engine.
Figure 17:
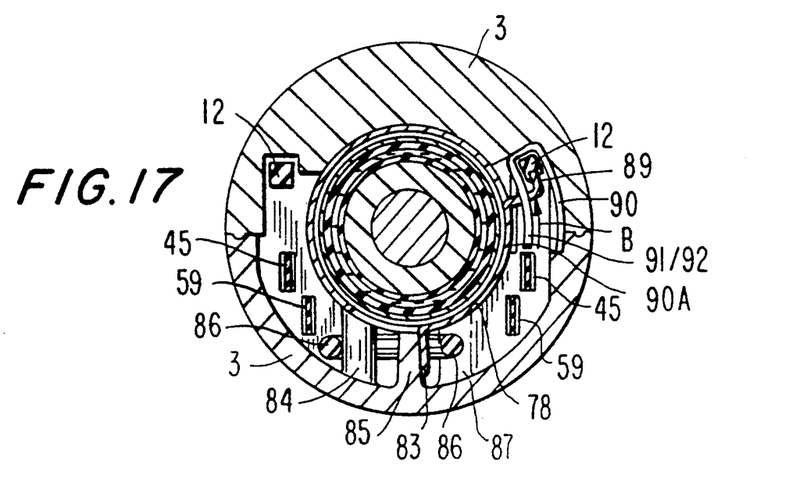
FIG. 17 is a view similar to FIG. 16, except that it depicts the coupler after the drive belt is coupled to the engine.
Figure 18:
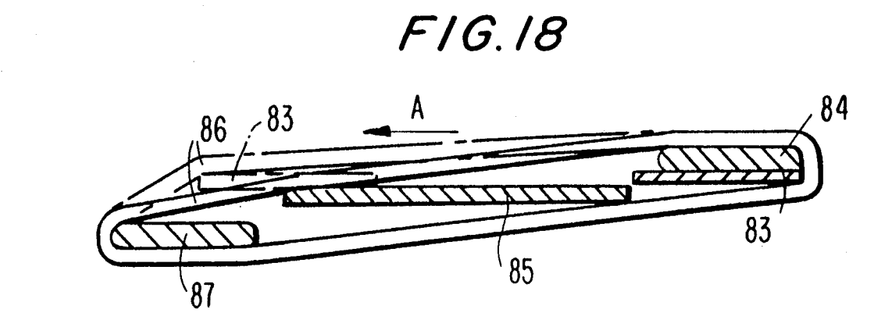
FIG. 18 is a schematic sectional view illustrating the movement of certain features of the coupler (as shown in FIG. 11) as the coupler is activated.
Figure 19:
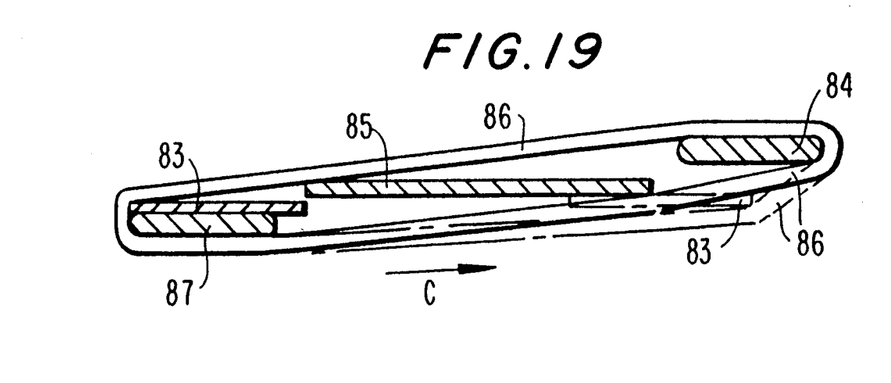
FIG. 19 is similar to FIG. 18, except that it illustrates movement of certain features of the coupler as the coupler is deactivated.

Referring specifically to FIGS. 18 and 19, the operation of this arrangement is explained in detail. Before pressure is applied to spring 69 in engine 6, outwardly directed tab 83, located on the outside surface of coupling sleeve 78, rests against post 84, mounted on the inside surface of the housing 3 (FIG. 16). During the engine's spring compression cycle—i.e., when fluid pressure is applied to engine 6 and belt 12 is in a disengaged state—coupling sleeve 78 is driven to the distal end of device 1. This movement causes tab 83 to slide parallel to rail 85 in the direction indicated by arrow A (FIG. 18). Rail 85 is mounted on the inside surface of housing 3. Just before tab 83 clears rail 85 (shown in phantom lines in FIG. 18), tab 83 engages elastic band 86, which presses the tab against the rail. When the trailing end of tab 83 clears the distal end of rail 85, the tab is forced by elastic band 86 to rest against second post 87. The movement of tab 83 over to post 87 causes the rotation of sleeve 78. Referring to FIG. 17, rotation of sleeve 78 in the direction of arrow B causes toothed tabs 88 and 89 to engage drive belt 12. Drive belt 12 is thus temporarily coupled to engine 6. When the power stroke, as explained above, begins, sleeve 78 moves in the proximal direction and belt 12 moves with it due to the engagement of toothed tabs 88 and 89. The movement of sleeve 78 is sufficient to rotate needle 5 360° in one power stroke.

Referring again to FIG. 19, the proximal movement of coupling sleeve 78 also causes tab 83 to slide parallel to rail 85 in the direction of arrow C to the position shown in phantom lines. Pressure derived from the engagement of tabs 88 and 89 with belt 12 holds tab 83 against rail 85. Before tab 83 clears rail 85, tab 83 once again engages elastic band 86 which further presses tab 83 against rail 85. When the trailing end of tab 83 clears the proximal end of rail 85, the tab is forced over to post 84, where it comes to rest in its original position. As before, this action rotates coupling sleeve 78. However, now sleeve 78 rotates in the opposite direction of arrow B in FIG. 17, releasing toothed tabs 88 and 89 from drive belt 12 and uncoupling the belt from spring 69 (FIG. 16).

Referring to FIGS. 16 and 17, contained within coupler 7 is a sled 90. The purpose of sled 90 is to reduce the drag on drive belt 12 against housing 3 by providing a lubricated sliding surface for the clamped belt, as well as to provide a surface against which the belt can be clamped. Sled 90 is connected to coupling sleeve 78 by sled extensions 91 and 92 which are positioned between tabs 88 and 89. A third extension 90A, located between extensions 91 and 92, position sled 90 between coupling sleeve 78 and housing 3. When coupling sleeve 78 rotates, just prior to the engine's power stroke, tabs 88 and 89 clamp belt 12 to sled 90. This allows belt 12 to travel with sled 90 as spring 69 is released from its compressed state. When drive belt 12 is unclamped, belt 12 is free to slide through sled 90 as it passes through coupler 7.

Referring to FIGS. 13 and 14, full extension of spring 69 during the engine's power stroke is regulated by a clip 70 mounted on the distal end of connecting rod 71. Clip 70 engages a washer 72 which in turn engages the inside wall of the proximal end of engine housing 73. Clip 70 ensures that all primary engine parts connected to rod 71 will return to their predetermined starting positions, and that needle 5 will only rotate through a prescribed stroke distance. Washer 72, slideably mounted on connecting rod 71, acts as a buffer between the small surface area of clip 70 and the larger surface area of the proximal end of engine housing 73. Washer 72 has the secondary function of removing any biological debris from connecting rod 71 before it leaves engine housing 73 so the debris does not enter engine 6 or coupler 7. The distal end of connecting rod 71 is slideably secured within passage 74, located at the distal end of engine housing 73. This positions connecting rod 71 within the engine assembly. Engine housing 73 is designed with an aperture to provide access to clip 70, connecting rod 71, and washer 72.

In order to provide greater flexibility in locating sutures with the invention, a head articulation system is provided. This system will be explained below with reference to FIGS. 1 and 7–11. As shown in FIG. 8, when head 2 is in a "resting" position, needle 5 lies in a plane angled at approximately 45° from the longitudinal axis of device 1. The "resting" position of head 2 allows the device to be inserted and removed from a patient's body cavity through a cannula. However, with the articulation system, the position of head 2 may be rotated about any of the three axes (x, y and z, shown in FIG. 1). Thus, the position of head 2, and needle 5 therein, can be changed to accommodate almost any suturing angle.

Two "timing" belts 45 and 59 are provided for controlling the movement of the head about the x and y axes. As shown in FIG. 11, in a preferred embodiment, both timing belts 45 and 59 are toothed on both sides. This provides for positive engagement of belts 45 and 59 with sprocketed bases 46 and 60, respectively. It also provides a user of the device with a gripping surface on the outside of each belt. Alternatively, belts 45 and 59 can be provided with other gripping means including a rough outer surface or slits. Another alternative, is to employ standard timing belts 45 and 59 having teeth on the inside only. Belts 45 and 59 can then be turned inside out beyond guiding channel 35B (FIG. 8) after the belts have exited head 2. The belt teeth will therefore be exposed to a user for gripping at the proximal end of the device.

As will be appreciated, head 2 can also be rotated about a longitudinal axis passing through the center of suturing device 1 (the z-axis) simply by rotating suturing device 1 within cannula 4. Alternatively, head 2 can be mounted for independent rotation from device 1 about the z-axis.

Belt 45 controls rotation of head 2 about the x-axis, specifically an axis passing through the center of rotation of axles 26 and 29 (FIG. 7). At the proximal end of the device, belt 45 is supported by pulley 44. As best shown in FIGS. 8 or 10, a sprocketed base 46 engages and supports belt 45 at the distal end of the device. Fixed to the top of base 46 is a worm gear 50 which, together with base 46, is rotationally mounted on post 51. This assembly is held in place by a washer 52 and a circle clip 53 which is received in groove 53A. Worm gear 50 meshes with a mating worm wheel 54 (FIG. 9), which is pivotally mounted on x-axis bearing extensions 56 and 57 by axles 26 and 29. Translational movement of x-axis timing belt 45 thus rotates worm gear 50, which in turn engages and rotates worm wheel 54 and finally rotates head 2 about the x-axis.

Similar to x-axis timing belt 45, timing belt 59 controls rotation of head 2 about the y-axis, specifically an axis passing through the center of rotation of post 51, as shown in FIG. 8. Y-axis timing belt 59 is also supported by a pulley 58 at the proximal end of device 1. At the distal end of the device belt 59 engages and is supported by sprocketed base 60. Sprocketed base 60 is fixed to bearing extensions 56 and 57 (which are part of detent plate 49) and rotates around the y-axis on post 51. Through this arrangement, translational movement of y-axis timing belt 59 is thus converted into rotational movement of head 2 about the y-axis.

It should be noted that manipulation of belt 59 by itself will also affect the position of head 2 about the x-axis. Thus, if articulation of head 2 is required only about the y-axis, with no change of position about the x-axis (i.e., the head has already been properly positioned about the x-axis), then belts 45 and 59 should be operated simultaneously. This will allow head 2 to move about the y-axis without any change in the position of the head about the x-axis. Alternatively, means for articulating the head in more than one direction by a single control element is contemplated.

As best shown in FIG. 10, detent plate 49 is mounted on post 51, between the post and sprocketed base 60. Small protrusions 47 on the bottom of base 46 are sequentially received in detents 48 located on the top surface of detent plate 49. This provides a user with a tactile output, in the form of a "click," which allows the user to gauge the relative rotational movement between base 46 and plate 49 when head 2 is rotated about either the x-axis or y-axis.

Figure 15:
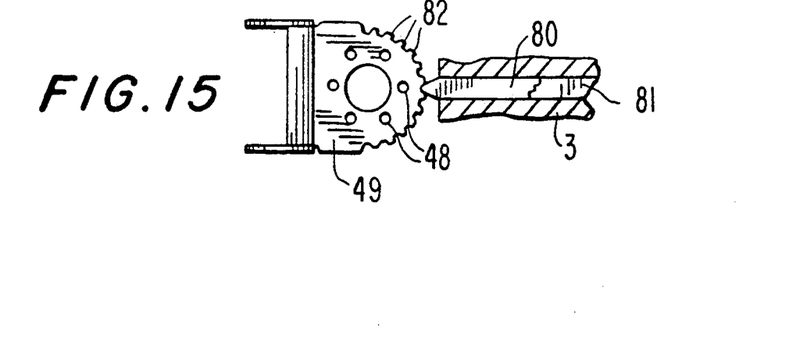
FIG. 15 is a partial section view taken along line 15—15 of FIG. 13, showing the follower and the detent plate.

In order to lock head 2 into position to prevent unwanted movement of the head as a suture is installed, an automatic locking system is provided. Referring to FIGS. 14 and 15, protruding from the distal end of engine housing 73 is a follower 80 slideably mounted in groove 81 formed on the inside surface of housing 3. Follower 80 is fixed to engine housing 73, or alternatively, is a separate piece butted up against engine housing 73. Whenever a sufficient amount of pressure is present within cylinder 65 (during either the spring compression cycle or the engine's power stroke) a force is imparted on follower 80 through engine housing 73. This force secures the tip of follower 80 in between crests 82 formed on detent plate 49, and rigidly secures the position of head 2. By restricting movement of head 2, proper placement of a suture is ensured.

As explained above, when at rest, the foot pedal assembly provides a small pressure force to the engine. This force keeps follower 80 in contact with detent plate 49, but still allows the follower to ride crests 82 on detent plate 49 when head 2 is articulated about the y-axis. Sufficient clearance room is provided between the proximal end of piston 67 and cylinder opening 64 to allow follower 80 to ride crests 82, as best illustrated in FIG. 13.

Referring to FIGS. 6–8 and 10, mounted to a front face 94 of saddle 13 is a capstan-like post 95. Post 95 is separated from front face 94 by a gap which allows thread 92 to pass therebetween while needle 5 rotates on saddle 13. Capstan-like post 95 has rounded edges which helps to secure the pre-looped suture thread to head 2 during the suturing process, but also allows thread 92 to be easily removed from head 2 when a user is prepared to tie a knot to secure a suture. Located in the top portion of front face 94 is an aperture 91. Aperture 91 is utilized to lay up suture thread 92 before suturing. It allows a loop of thread 92 to be drawn up the length of suturing device 1 so that some of the thread manipulation may be done outside the internal body cavity of a patient.

Preferably, surgical suturing device 1 is contained within a kit. This kit comprises a trocar and the surgical suturing device described herein, configured and dimensioned to be inserted into the trocar cannula. The elements of the kit are immersed in a medically safe lubricant which not only provides for easier movement of the mechanical parts within suturing device 1, but also, eases insertion of the suturing device into the trocar cannula.

Figure 5:
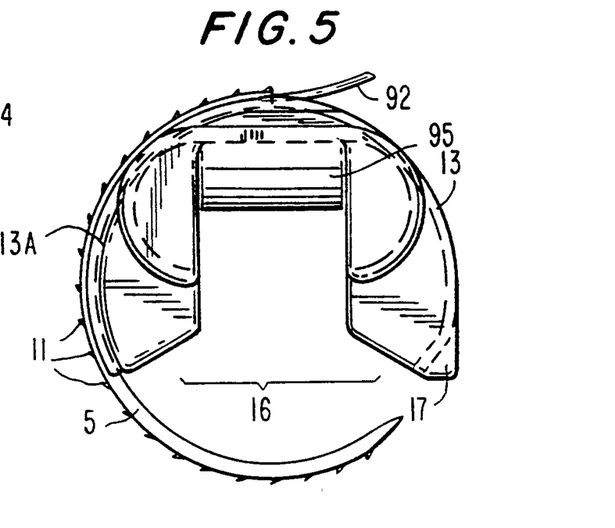
FIG. 5 is a view similar to FIG. 2, except that it shows the barbed arcuate suturing needle rotated partially out of the saddle.
Figure 6:
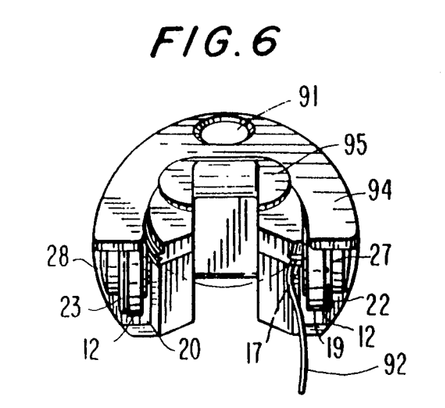
FIG. 6 is a front end view of the head (proximal end) of the surgical suturing device according to the invention.

The surgical suturing device described herein is equally well suited and adaptable for ligating a biological tube or duct. Referring to FIG. 5, needle 5 is simply passed around or through the tube or duct accommodated in opening 16, after which, the resulting knot is secured.

Except as specifically noted, the various components of the present invention may be constructed from a variety of biocompatible materials, particularly plastics, the specific selection of which is well within the ability of a person of ordinary skill in the art.

I claim:

1. An apparatus for suturing or ligating, comprising:
   a body member having first and second ends;
   at least two rotatable pulleys mounted within the body member;
   a flexible, continuous loop drive element mounted on said pulleys for circulation therearound;
   means mounted in the body member adjacent to the first end for circulating the continuous loop element; and
   an arcuate suturing needle mounted at the second end of the body member for 360° rotation through a closed path, said needle having a plurality of spaced projecting means for engaging the continuous loop element over an included segment of the needle's outer perimeter.

2. The apparatus of claim 1, wherein said projecting means are arranged on the needle such that at least two of said projecting means engage the continuous lop element at all times during rotation of the needle.

3. The apparatus of claim 1, further comprising rotatable means for supporting the continuous loop drive element adjacent to the first end, wherein said means for supporting extends at least partially outside of the body member to allow direct manipulation of the drive element by a user, whereby positioning of the needle may be controlled by hand.

4. The apparatus of claim 1, wherein the arcuate needle defines an arc having an included angle greater than 180°, and wherein said apparatus further comprises:
   a saddle member mounted at the second end having arcuate outer surface slideably mating with and received inside the arc of the arcuate needle, said outer surface defining an arc also having an included angle greater than 180°, said saddle member further defining an open throat area opposite said outer surface of the saddle in which material to be sutured is received; and
   means for tensioning said continuous loop drive element around the arcuate outer surface with the needle received therebetween such that the needle projecting means are maintained in engagement with the continuous loop drive element.

5. The apparatus of claim 1 wherein said circulating means comprises:
   a reciprocating member slideably mounted within the housing for longitudinal movement therein; and
   means for coupling said continuous loop element with the reciprocating member during movement of said member in a first longitudinal direction and for uncoupling said element from the reciprocating member during movement in a second opposite longitudinal direction.

6. The apparatus of claim 5, wherein said coupling means comprises:
   a coupling sleeve engaging the reciprocating member for longitudinal movement therewith and being freely rotatable therearound;
   means projecting from the sleeve for engaging said continuous loop element; and
   means for rotating the coupling sleeve (a) in a first rotational direction in response to said longitudinal movement of the reciprocating member in the second longitudinal direction whereby said means projecting from the sleeve engages the continuous loop element for movement in the first longitudinal direction and (b) in a second opposite rotational direction in response to longitudinal movement of the reciprocating member in the first longitudinal direction whereby said means projecting from the sleeve disengages the continuous loop element.

7. The apparatus of claim 5, wherein:
   said body member comprises an elongated housing and a head assembly pivotally mounted on the elongated housing at the second end, wherein the arcuate needle is mounted in the head assembly and said head assembly is capable of rotational movement independent from said elongated housing; and
   said apparatus further comprises means for locking the position of the head assembly, said locking means cooperating with said circulating means to lock the head assembly during suturing or ligating procedures.

8. The apparatus of claim 1, further comprising internal sealing means to prevent the escape of pressure from an internal body cavity during suturing or ligating procedures.

9. An apparatus for suturing or ligating, comprising:
   an elongated housing defining a central longitudinal axis having first and second ends;
   a continuous loop drive element mounted within the body member for circulation therein;
   means mounted in the body member adjacent to the first end for circulating the continuous loop element; and
   an arcuate suturing needle mounted at the second end of the body member for 360° rotation through a closed path, said needle having a plurality of spaced projecting means for engaging the continuous loop element over an included segment of the needle's outer perimeter; and
   a head assembly pivotally mounted on the elongated housing at the second end, wherein the arcuate needle is mounted in the head assembly and said head assembly is capable of rotational movement independent from said elongated housing and around at least one axis disposed at an angle to the longitudinal axis.

10. The apparatus of claim 9, further comprising means for articulating said head assembly independently from said elongated housing, said means for articulating comprising at least one elongated drive element rotatably mounted within said housing and being manipulable at the first end of the housing.

11. The apparatus of claim 10, wherein said means for articulating the head assembly further comprises:
- pulley means for supporting the elongated drive element at the second end, said pulley means being rotatable about a second axis transverse to the longitudinal axis in response to manipulation of the drive element at the first end;
- a worm gear mounted at the second end of the housing for rotation with said pulley means; and
- a worm wheel comprising a portion of the head assembly mounted for rotation around a third transverse axis and cooperating with the worm gear, whereby manipulation of the drive element causes the head assembly to pivot around said third axis due to said cooperation of the worm gear and worm wheel.

12. The apparatus of claim 10, wherein said means for articulating the head assembly further comprises:
- pulley means for supporting the elongated drive element at the second end, said pulley means being rotatable about a second axis transverse to the longitudinal axis in response to manipulation of the drive element at the first end; and
- a bracket member mounted at the second end for rotation with said pulley means, the head assembly being carried by said bracket member, whereby manipulation of the drive element causes the head assembly to pivot around said second axis.

13. An apparatus for suturing or ligating, comprising:
- an elongated housing defining a first longitudinal axis and having first and second ends;
- a head assembly pivotally mounted at the second end of the housing, said head being capable of pivoting about second and third axes independently from the elongated housing;
- a continuous loop drive element mounted within the housing and said head assembly for circulation therethrough;
- an arcuate needle mounted within the head assembly for 360° rotation in a closed path, said needle having a plurality of spaced projecting means for engaging said continuous element;
- means for articulating the head assembly independently about the second or third axes independently from said elongated housing;
- means for circulating the continuous loop drive element.

14. The apparatus of claim 13, wherein said means for pivoting the head assembly comprises:
- a first elongated drive element rotatably mounted within said housing and being manipulable at the first end of the housing;
- first pulley means for supporting the first elongated drive element at the second end, said pulley means being rotatable about a second axis transverse to the longitudinal axis in response to manipulation of the first drive element at the first end;
- a bracket member mounted at the second end for rotation with said pulley means, the head assembly being carried by said bracket member, whereby manipulation of the first drive element causes the head assembly to pivot around said second axis;
- a second elongated drive element rotatably mounted within said housing and also being manipulable at the first end of the housing;
- second pulley means for supporting the second elongated drive element at the second end, said second pulley means also being rotatable about the second axis in response to manipulation of the second drive element at the first end;
- a worm gear mounted at the second end of the housing for rotation with said second pulley means; and
- a worm wheel comprising a portion of the head assembly mounted for rotation around a third transverse axis and cooperating with the worm gear, whereby manipulation of the second drive element causes the head assembly to pivot around said third axis due to said cooperation of the worm gear and worm wheel.

15. The apparatus of claim 13 wherein, said means for circulating the continuous loop drive element further comprises:
- a reciprocating member slideably mounted within the housing for longitudinal movement therein;
- biasing means cooperating with an end of the reciprocating member for biasing said member in a first direction;
- cylinder means cooperating with the opposite end of the reciprocating member for forcing said member in a second direction against said biasing means;
- means for actuating and de-actuating said cylinder means; and
- means for coupling said continuous loop element with the reciprocating member during movement of said member in the first longitudinal direction and for uncoupling said element during movement in the second opposite longitudinal direction.

16. An apparatus for suturing or ligating, comprising:
- a body member having first and second ends;
- a continuous loop drive element mounted within the body member for circulation therein;
- rotatable means for supporting the continuous loop drive element wherein said rotatable means is carried by a longitudinally sliding member within the housing, said sliding member being biased in the direction of the first end to maintain tension in the continuous loop drive element, and said continuous loop drive element is manipulable at the first end of the housing;
- means mounted in the body member adjacent to the first end for circulating the continuous loop element; and
- an arcuate suturing needle mounted at the second end of the body member for 360° rotation through a closed path, said needle having a plurality of spaced projecting means for engaging the continuous loop element over an included segment of the needle's outer perimeter.

17. A mechanical apparatus for suturing tissue or ligating a biological tube or duct, comprising:
- an elongated housing, defining a first longitudinal axis and having first and second ends;
- a head assembly pivotally mounted at the second end of the housing, said head being capable of pivoting about second and third axes independently from the elongated housing;
- a continuous loop drive element mounted within the housing and head assembly for circulation therethrough;
- an arcuate needle mounted within the head assembly for 360° rotation through a closed path, said needle defining an arc having an included angle greater than 180°, and having a plurality of closely spaced projecting means for engaging the continuous loop drive element, said projecting means arranged on the needle such that at least two of said projecting means engage the continuous loop element at all times during rotation of the needle;

a saddle member mounted at the second end of the housing having an arcuate outer surface slideably mating with and received inside the arc of the arcuate needle, said outer surface defining an arc having an included angle greater than 180°, said saddle member further defining an open throat area opposite said outer surface of the saddle in which material to be sutured is received;

means for tensioning said continuous loop drive element around the arcuate outer surface of said saddle member with said needle received therebetween such that the needle projecting means are maintained in engagement with the continuous loop drive element;

means for articulating the head assembly independently about the second or third axes, said means comprising;

a first elongated drive element rotatably mounted within said housing and being manipulable at the first end of the housing, first pulley means for supporting the first elongated drive element at the second end, said pulley means being rotatable about a second axis transverse to the longitudinal axis in response to manipulation of the first drive element at the first end, a bracket member mounted at the second end for rotation with said pulley means, the head assembly being carried by said bracket member, whereby manipulation of the drive element causes the head assembly to pivot around said second axis, and a second elongated drive element rotatably mounted within said housing and also being manipulable at the first end of the housing, second pulley means for supporting the second elongated drive element at the second end, said second pulley means also being rotatable about the second axis in response to manipulation of the second drive element at the first end, a worm gear mounted at the second end of the housing for rotation with said second pulley means, and a worm wheel comprising a portion of the head assembly mounted for rotation around a third transverse axis and cooperating with the worm gear, whereby manipulation of the second drive element causes the head assembly to pivot around said third axis due to said cooperation of the worm gear and worm wheel;

means for circulating the continuous loop drive element, said means comprising a reciprocating member slideably mounted within the housing for longitudinal movement therein, a coupling sleeve engaging the reciprocating member for longitudinal movement therewith and being freely rotatable therearound, means projecting from the sleeve for engaging said continuous loop drive element, and means for rotating the coupling sleeve (a) in a first rotational direction in response to said longitudinal movement in the second longitudinal direction whereby said means projecting from the sleeve engages the continuous loop element during movement in the first longitudinal direction and (b) in a second opposite rotational direction in response to longitudinal movement of the reciprocating member in the first longitudinal direction whereby said means projecting from the sleeve disengages the continuous loop element during movement in the second longitudinal direction; and means for locking the position of the head assembly during suturing or ligating procedures.

18. A kit for suturing tissue or ligating a tube or duct within a body cavity, comprising:
a cannula adapted to be inserted through the body wall and communicate with the cavity; and
a mechanical apparatus for suturing or ligating configured and dimensioned to be slidingly received in said cannula in a gas-tight manner, said apparatus comprising
an elongated housing having first and second ends and a head assembly pivotally mounted on the elongated housing at the second end, wherein said head assembly is capable of articulation ;independent from said elongated housing and is articulable from a position outside the cannula at the first end of the elongated housing;
a continuous loop drive element mounted within the body member for circulation therein;
means for circulating the continuous loop element; and
an arcuate needle mounted for rotation within the head assembly having a plurality of spaced projecting means for engaging the continuous loop drive element.

19. The kit of claim 18, wherein the apparatus for suturing or ligating further comprises rotatable means for supporting the continuous loop drive element adjacent to the first end, said means extending at least partially outside of the elongated housing to allow direct manipulation of the drive element by a user, whereby positioning of the needle may be controlled by hand from a position outside the cannula adjacent to the first end.

20. The kit of claim 18, wherein the apparatus for suturing or agating further comprises internal sealing means to prevent the escape of pressure from an internal body cavity during suturing or ligating procedures.

21. A kit for suturing or ligating, including in combination:
a trocar comprising a cannula having a length and a stylet adapted to be slideably received in the cannula and extend beyond the cannula, said cannula having sealing means for providing a gas-tight seal around said stylet when received in the cannula; and
a mechanical suturing apparatus, comprising
an elongated housing defining a first longitudinal axis and having first and second ends,
a head assembly pivotally mounted at the second end of the housing, said head being capable of pivoting about second and third axes independently from the elongated housing, wherein the housing and head assembly are configured and dimensioned to be slidingly received in the cannula and together have a length greater than said cannula length,
a continuous loop drive element mounted within the housing and head assembly for circulation therethrough,
an arcuate needle mounted within the head assembly for 360° rotation in a closed path, said needle having a plurality of spaced projecting means for engaging said continuous loop drive element,
means manipulable by hand when the housing and head assembly are received in the cannula for pivoting the head assembly about the second or third axes independently from said elongated housing, and
means for circulating the continuous loop drive element.

* * * * *